US009377416B2

(12) United States Patent
Maleev et al.

(10) Patent No.: US 9,377,416 B2
(45) Date of Patent: Jun. 28, 2016

(54) WAFER EDGE DETECTION AND INSPECTION

(71) Applicant: KLA-Tencor Corporation, Milpitas, CA (US)

(72) Inventors: Ivan Maleev, Pleasanton, CA (US); Venkata Kode, Hayward, CA (US)

(73) Assignee: KLA-Tencor Corp., Milpitas, CA (US)

( * ) Notice: Subject to any disclaimer, the term of this patent is extended or adjusted under 35 U.S.C. 154(b) by 0 days.

(21) Appl. No.: 14/709,427

(22) Filed: May 11, 2015

(65) Prior Publication Data

US 2015/0330914 A1    Nov. 19, 2015

Related U.S. Application Data

(60) Provisional application No. 61/994,835, filed on May 17, 2014.

(51) Int. Cl.
*G01N 21/00* (2006.01)
*G01N 21/95* (2006.01)
*G01N 21/55* (2014.01)
*G01N 21/47* (2006.01)

(52) U.S. Cl.
CPC ............ *G01N 21/9503* (2013.01); *G01N 21/47* (2013.01); *G01N 21/55* (2013.01); *G01N 2201/025* (2013.01); *G01N 2201/061* (2013.01)

(58) Field of Classification Search
CPC ............................... G01N 21/00; G01N 21/47
USPC ..................................................... 356/237.5
See application file for complete search history.

(56) References Cited

U.S. PATENT DOCUMENTS

| 4,402,607 | A  | 9/1983  | McVay et al. |
| 5,822,213 | A  | 10/1998 | Huynh |
| 7,280,197 | B1 | 10/2007 | Rosengaus |
| 7,728,965 | B2 | 6/2010  | Haller et al. |
| 7,768,637 | B2 | 8/2010  | Schupp et al. |

(Continued)

FOREIGN PATENT DOCUMENTS

| JP | 2008-203151 | 9/2008 |
| JP | 2008-311302 | 12/2008 |

OTHER PUBLICATIONS

International Search Report for PCT/US2015/031051 mailed Aug. 27, 2015.

(Continued)

*Primary Examiner* — Roy M Punnoose
(74) *Attorney, Agent, or Firm* — Ann Marie Mewherter

(57) ABSTRACT

Methods and systems for determining wafer inspection coordinates for fixed location(s) on a wafer are provided. One system includes an illumination subsystem configured to direct light to a spot on an edge of a wafer. The spot extends beyond the edge of the wafer. The system also includes a stage that rotates the wafer thereby causing the spot to be scanned over the edge of the wafer. The system also includes a detector configured to detect light from the spot while the spot is being scanned over the edge and to generate output responsive thereto. The system further includes a computer processor configured to determine wafer inspection coordinates of two or more locations on the edge of the wafer based on the output and to determine wafer inspection coordinates of fixed location(s) on the wafer based on the wafer inspection coordinates of the two or more locations on the edge.

22 Claims, 3 Drawing Sheets

(56) References Cited

U.S. PATENT DOCUMENTS

| | | |
|---|---|---|
| 8,325,334 B2 | 12/2012 | Ramachandran et al. |
| 2004/0056216 A1* | 3/2004 | Inenaga ............... G03F 9/7011 250/548 |
| 2008/0259326 A1* | 10/2008 | Kutscher ............ G01N 21/4738 356/237.5 |
| 2008/0309927 A1 | 12/2008 | Grueneberg |
| 2013/0236085 A1 | 9/2013 | Chen et al. |

OTHER PUBLICATIONS

Tai et al., "A Fast Algorithm for Single Image Super Resolution in Both Wavelet and Spatial Domain," 2012 International Symposium on Computer, Consumer and Control, Jun. 4-6, 2012, pp. 702-705.

* cited by examiner

WAFER EDGE DETECTION AND INSPECTION

BACKGROUND OF THE INVENTION

1. Field of the Invention

This invention generally relates to methods and systems for wafer edge detection and inspection.

2. Description of the Related Art

The following description and examples are not admitted to be prior art by virtue of their inclusion in this section.

Inspection processes are used at various steps during a semiconductor manufacturing process to detect defects on wafers to promote higher yield in the manufacturing process and thus higher profits. Inspection has always been an important part of fabricating semiconductor devices. However, as the dimensions of semiconductor devices decrease, inspection becomes even more important to the successful manufacture of acceptable semiconductor devices because smaller defects can cause the devices to fail.

Information beyond simple defect detection is often not generated during inspection processes. For example, defect characteristics such as size, magnitude, and location may be determined based on information generated by wafer inspection. However, such information is typically not sufficient to determine defect classifications. Therefore, after wafer inspection, additional information for the defects detected by inspection may be generated using a defect review tool and defect classification is then determined based on the additional information. In some such instances, defects found by an optical defect finding apparatus may be reviewed using a high resolution scanning electron microscope (SEM) review tool.

In order for the defect review to be successful, it is necessary to know the locations of the defects detected by inspection with relatively high accuracy with respect to some fixed location on the wafer. For example, during wafer inspection, the defect coordinates may be determined with respect to a fixed location on a wafer. Therefore, once the wafer is transferred from the wafer inspection system to the defect review tool, the defects can be found by the defect review tool based on the coordinates reported by the wafer inspection system and the fixed location identified by the defect review tool. The fixed location on the wafer can be a center of the wafer and/or a notch formed in the edge of the wafer. As such, determining the coordinates of such fixed locations with substantially high precision during inspection can substantially reduce the difficulty of finding the defects during defect review.

Some methods used by wafer inspection systems for detecting an edge and a notch of a wafer are based on multiple scans and are compatible with wafer inspection tool architectures that scan a spot in a spiral manner over a wafer. In those architectures, wafers may spin up to 100 rotations per second. The wafer inspection systems may utilize an illumination spot with a size ranging from a few microns to tens of microns. Optical collection subsystems of such systems may collect light scattered by the wafer surface and detect the presence of defects of interest (DOI) on the wafer based on changes in the scattering signal. In order to achieve minimum inspection time, the spot path on a wafer is a spiral track with the pitch of a spiral defined by spot size.

The relatively small pitch of a spiral track allows the edge detection system to collect data over multiple revolutions without impacting tool throughput. The same considerations make a single relatively high speed photosensitive element a natural choice for currently used edge detection methods.

Alternative approaches used in some other wafer inspection and metrology tools rely on imaging sensors used to take a limited number of pictures or images of the wafer edge, e.g., 3 to 4. Edge coordinates are found in each of those images and are then used to calculate center of wafer coordinates. Notch detection may require either a whole wafer edge scan or preliminary information about notch position (e.g., from a pre-aligner). Such approaches are typically not integrated with the spiral scanning wafer inspection systems.

Edge detection systems that have edge inspection capability may provide users with additional value. However, currently used single-detector systems rely on gradual changes in detector signal over multiple tracks and therefore may have limited resolution, especially when compared to direct imaging systems, which limits their edge inspection capabilities. For example, a defect may manifest itself as a relatively small change in the signal of a single detector and therefore it would be difficult to detect while relying on gradual track-to-track changes in edge detector signal.

Accordingly, it would be advantageous to develop methods and systems for determining wafer inspection coordinates for one or more fixed locations on a wafer that do not have one or more of the disadvantages described above.

SUMMARY OF THE INVENTION

The following description of various embodiments is not to be construed in any way as limiting the subject matter of the appended claims.

One embodiment relates to a system configured to determine wafer inspection coordinates for one or more fixed locations on a wafer. The system includes a light source and at least one optical element forming an illumination subsystem configured to direct light to a spot on an edge of a wafer. The spot extends beyond the edge of the wafer such that a first portion of the spot impinges on the wafer and the edge of the wafer and a second portion of the spot does not impinge on the wafer or the edge of the wafer. The system also includes a stage configured to rotate the wafer thereby causing the spot to be scanned over the edge of the wafer. The wafer is rotated fewer than two times while the spot is scanned over the edge. In addition, the system includes a detector configured to detect light from the spot while the spot is being scanned over the edge and to generate output responsive to the detected light. The system further includes a computer processor configured to determine wafer inspection coordinates of two or more locations on the edge of the wafer based on the output and to determine wafer inspection coordinates of one or more fixed locations on the wafer based on the wafer inspection coordinates of the two or more locations on the edge. The system may be further configured as described herein.

Another embodiment relates to a method for determining wafer inspection coordinates for one or more fixed locations on a wafer. The method includes directing light to a spot on an edge of a wafer. The spot extends beyond the edge of the wafer such that a first portion of the spot impinges on the wafer and the edge of the wafer and a second portion of the spot does not impinge on the wafer or the edge of the wafer. The method also includes rotating the wafer thereby causing the spot to be scanned over the edge of the wafer. The wafer is rotated fewer than two times while the spot is scanned over the edge. In addition, the method includes detecting light from the spot while the spot is being scanned over the edge to thereby generate output responsive to the detected light. The method further includes determining wafer inspection coordinates of two or more locations on the edge of the wafer based on the output and determining wafer inspection coordinates of one or more fixed locations on the wafer based on the wafer inspection coordinates of the two or more locations on the edge. The determining steps are performed by a computer processor.

Each of the steps of the method described above may be performed as described further herein. The method described above may include any other step(s) of any other method(s) described herein. The method described above may be performed using any of the systems described herein.

BRIEF DESCRIPTION OF THE DRAWINGS

Other objects and advantages of the invention will become apparent upon reading the following detailed description and upon reference to the accompanying drawings in which.

Figure 1:
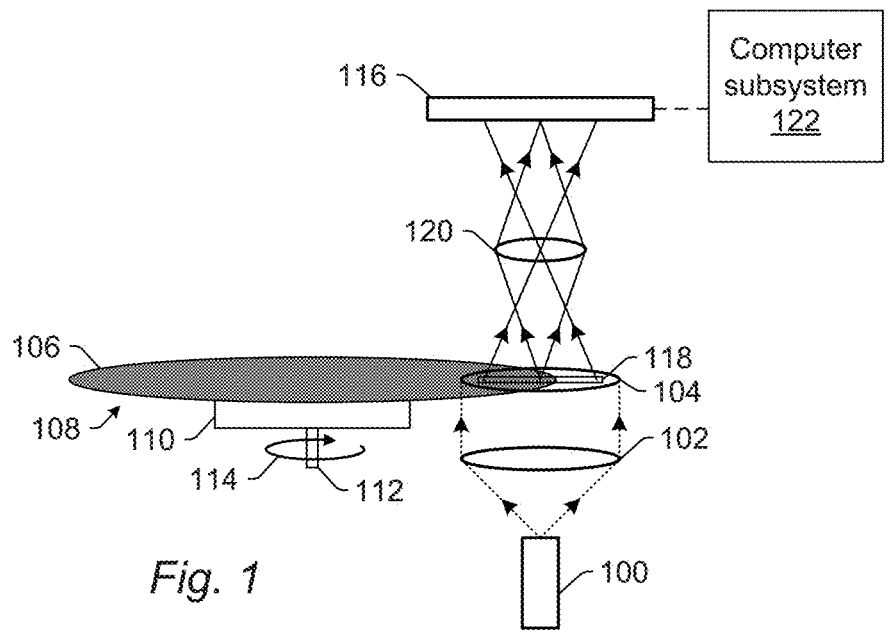
FIGS. 1-2 are schematic diagrams illustrating side views of embodiments of a system configured as described herein.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Turning now to the drawings, it is noted that the figures are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals. Unless otherwise noted herein, any of the elements described and shown may include any suitable commercially available elements.

The embodiments described herein generally relate to wafer edge detection and possibly inspection. The embodiments described herein may therefore be referred to as edge and notch detection modules (or ENDMs).

One embodiment relates to a system configured to determine wafer inspection coordinates for one or more fixed locations on a wafer. The system includes a light source and at least one optical element forming an illumination subsystem configured to direct light to a spot on an edge of a wafer. One embodiment of such a system is shown in FIG. 1. This system embodiment includes light source 100 and optical element 102 forming an illumination subsystem configured to direct light to spot 104 on edge 106 of wafer 108. In one embodiment, the light source may be a light emitting diode (LED) that generates single wavelength light having a wavelength of, for example, 405 nm or 525 nm. LEDs suitable for use in the embodiments described herein may be commercially available from, for example, Thorlabs, Inc., Newton, N.J. The light source may, however, include any other suitable light sources known in the art including monochromatic, polychromatic, and broadband light sources. The wavelength(s) of light suitable for use in the embodiments described herein include, but are not limited to, visible wavelength(s) of light. The type of light source used in the system may be selected as described further herein and based on the information about the wafer that is to be generated by the system and/or wafer characteristic(s). For example, broadband illumination may be preferred in some instances to minimize sensitivity to reflective variation on the wafer and speckle effects.

The spot extends beyond the edge of the wafer such that a first portion of the spot impinges on the wafer and the edge of the wafer and a second portion of the spot does not impinge on the wafer or the edge of the wafer. In this manner, the spot may be separated into two different portions based on where the edge is located within the spot. As such, the spot may be essentially bisected by the edge. As described further herein, therefore, light from only one portion of the spot will be detected by the detector of the system. Therefore, some of the power of the illumination will be lost, but such power loss will be acceptable on a shot-noise limited system.

The spot may be positioned on the wafer (e.g., via movement of the wafer under the spot) such that the center of the spot corresponds roughly with the edge of the wafer (variation from such a configuration is acceptable, but significant portions of the spot are preferably located on either side of the edge of the wafer such that the location of the edge within the spot can be determined with relatively high confidence as described further herein). Therefore, the configurations described herein are different from most edge inspection systems in that unlike edge inspection systems in which an insignificant portion of the illumination may extend beyond the edge of the wafer (only to ensure that the entire edge is inspected), the embodiments described herein are configured such that a non-insignificant portion of the spot extends beyond the edge of the wafer such that the coordinates of the edge can be determined with relatively high confidence as described further herein. In contrast, having the edge of the wafer be located near the outer edge of the illumination, as in most edge inspection systems, can cause difficulty in discerning the edge of the wafer from the edge of the illumination on the wafer thereby reducing the accuracy with which the edge can be detected (if at all).

In one embodiment, the spot has at least one dimension greater than 2 mm. For example, the embodiments described herein may be configured to illuminate the edge of the wafer with a relatively large area (e.g., 2 mm to 10 mm in at least one dimension) "flood" or "line" illumination spot. A "flood" illumination spot is defined herein as a spot that has substantially large dimensions in two opposing directions and therefore may appear in the object plane to have a circular or oval (a relatively wide oval) shape. In contrast, a "line" illumination spot is defined herein as a spot that has substantially different dimensions in two opposing directions and therefore may appear in the object plane to have a linear type shape. In one particular example, the spot that is illuminated on the edge of the wafer may have a round shape and a diameter of about 10 mm.

In one embodiment, the light directed to the spot on the edge of the wafer includes substantially collimated light. In this manner, the light source described herein may be a collimated light source that is configured to send parallel (or substantially parallel) rays of light to one side of the wafer (the upper surface or the lower surface) with the light source being positioned on that same side of the wafer. For example, in the embodiment shown in FIG. 1, light source 100 is positioned below the wafer and the illumination subsystem is configured to direct light to the back side of the wafer. The "upper surface" or "front side" of the wafer is defined herein as the surface or side of the wafer on which devices are or will be formed. The "lower surface" or "back side" of the wafer is defined herein as the surface or side of the wafer on which devices are not and will not be formed.

Figure 2:
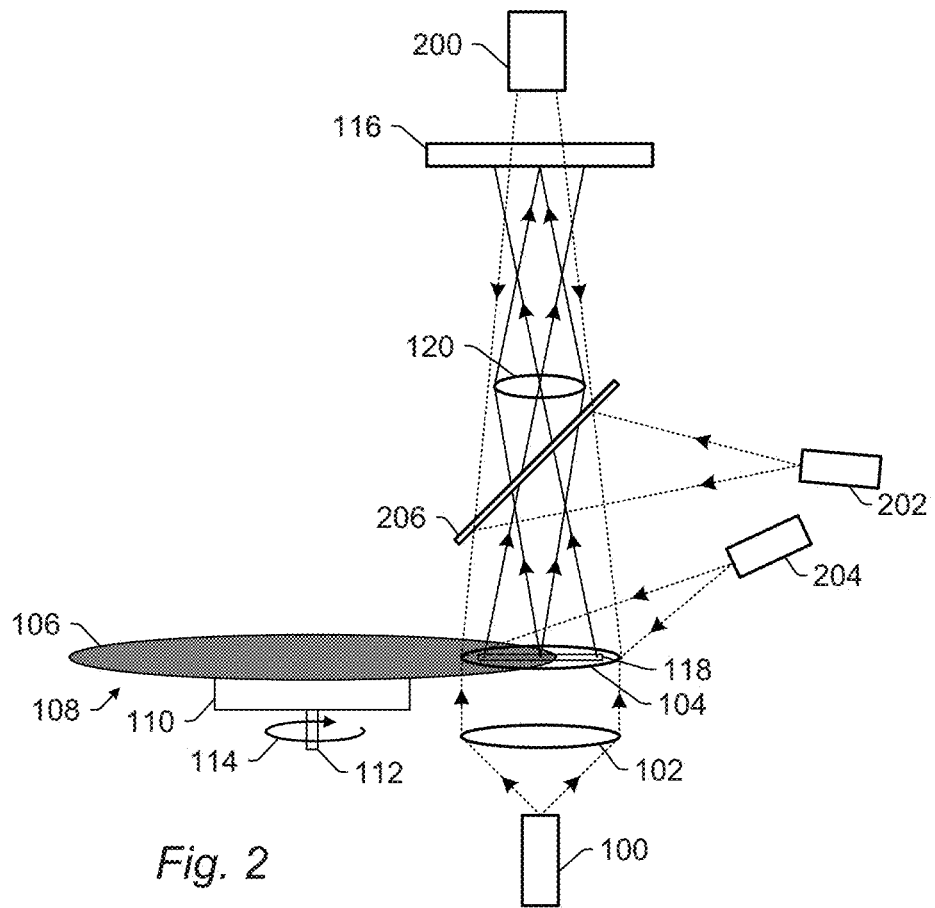

However, in other embodiments described herein, the light source may be positioned above the wafer and the illumination subsystem is configured to direct collimated or substantially collimated light to the front side of the wafer. For example, another embodiment of a system is shown in FIG. 2. In this embodiment, light source 200 is positioned above the wafer and the illumination subsystem is configured to direct light to the front side of the wafer. Light source 200 may include any of the light sources described herein such as an LED or any other suitable light sources known in the art. Although the light from light source 200 directed to the spot on the wafer is not shown in FIG. 2 as collimated light, the light source may generate collimated or substantially collimated light and/or may be coupled to one or more optical elements (not shown) that are configured to direct the light from the light source to the wafer as parallel or substantially parallel rays. As shown in FIG. 2, the system may include two different light sources, one to direct light to a back side of the wafer and another to direct light to a front side of the wafer. However, the system may include only light source 100 as shown in FIG. 1 or only light source 200 shown in FIG. 2. In addition, the system may include other combinations of two or more light sources. Therefore, the embodiments described herein may be configured to have one or more light sources that are configured to direct light to one or more sides of wafer.

In some embodiments, the light is directed to the spot at a normal angle of incidence. For example, light source 100 is, as shown in FIGS. 1 and 2, configured to direct light to optical element 102 that directs light to the spot at a normal angle of incidence. In another embodiment, the light is directed to the spot at an oblique angle of incidence. For example, light from light source 200 is, as shown in FIG. 2, configured to direct light to the spot at a substantially low angle of incidence (i.e., not normal illumination but possibly relatively close to normal illumination).

FIG. 2 also shows additional examples of light sources that may be included in the system. For example, the system may include light source 202 and/or light source 204. These light sources may include any suitable light sources known in the art. Light source 202 may be positioned as shown in FIG. 2 so that the light generated by this light source is directed to beam splitter 206. Beam splitter 206 may include any suitable beam splitter known in the art such as a 50/50 beam splitter. The beam splitter may be configured to direct light from light source 202 to spot 104 on the edge of the wafer at a normal or substantially normal angle of incidence. Beam splitter 206 may be configured as described further herein. In addition, light source 204 may be positioned as shown in FIG. 2 so that the light generated by this light source is directed to the spot on the edge of the wafer at an oblique angle of incidence, which may include any suitable oblique angle.

If the system embodiments described herein include more than one light source, those light sources may be configured differently or may have substantially the same configurations. For example, two or more of the light sources may have different makes and models. In addition, two or more of the light sources may be configured to generate light at different wavelengths. For example, one light source (e.g., light source 100) may be configured to generate light at a wavelength of 405 nm or 525 nm, while another light source (e.g., light sources 200, 202, and 204) may be configured to generate light at a different wavelength (e.g., 530 nm). In addition, one or more of the light sources may be configured to generate light having a polarization that is different than that of the light generated by the other light source(s). In any case, the characteristics of the light generated by any of the light sources described herein may be selected based on the characteristics of the side of the wafer that the light is directed to (e.g., the front side or the back side) as well as the function to be performed using the light (e.g., edge detection versus edge inspection).

Optical element 102 shown in FIG. 1 may be configured to direct the light to the spot on the edge in any suitable manner, e.g., as collimated light. Although the optical element is shown in FIG. 1 as a single refractive element, the optical element may be include one or more refractive optical elements and/or one or more reflective optical elements. In addition, the optical element may include any suitable optical element for directing the light from the light source to the spot on the edge of the wafer such as an aspheric condenser lens with a diffuser. Suitable optical elements for use in the illumination subsystems described herein may be obtained commercially from suppliers such as Thorlabs.

The illumination subsystem may include any other suitable optical elements (not shown) positioned in the path of the light generated by one or more of the light sources. Examples of such optical elements include, but are not limited to, polarizing component(s), spectral filter(s), spatial filter(s), reflective optical element(s), apodizer(s), beam splitter(s), aperture(s), and the like, which may include any such suitable optical elements known in the art. In addition, the system may be configured to alter one or more of the elements based on the type of illumination to be used. For example, the system may be configured to alter one or more characteristics of the illumination subsystem to alter the angle of incidence, polarization, wavelength, etc. used for inspection.

The embodiments described herein provide improved wafer edge and notch detection approaches and performance in spiral scanning wafer inspection tools. In particular, the system includes a stage configured to rotate the wafer thereby causing the spot to be scanned over the edge of the wafer. For example, as shown in FIG. 1, the system may include stage 110 coupled to shaft 112. The shaft may be coupled to one or more mechanical and/or robotic components that are configured to rotate the shaft as shown by arrow 114 thereby rotating the wafer in the same direction. The stage, shaft, and any other components coupled thereto may include any suitable such components known in the art.

The wafer is rotated fewer than two times while the spot is scanned over the edge. For example, in some cases, due to system architecture constraints, it may be desirable to perform edge and notch detection over a single wafer revolution. More specifically, next generation wafer inspection systems, which rely on multi-pixel sensors and imaging collection optics to improve resolution, may have a pitch between scan tracks that is larger than that of previous generation tools by orders of magnitude. For example, a sensor having 1000 pixels in one dimension with a projected 0.5 um pixel size on a wafer would command a pitch of about 500 um, compared to a 20 um single spot size on a previous generation system. That means that a wafer inspection scan only has 1-2 tracks near the edge, and the edge detection system has to perform its functions over a single track or risk not being able to operate concurrently with the main inspection system, thereby impacting system throughput. Therefore, relatively slow multi-channel edge inspection detectors with parallel acquisition of signal from multiple wafer locations become advantageous. In this manner, the embodiments described herein may be configured to detect the edge and/or notch of the wafer in a single pass.

It is noted that a single revolution of the wafer or a single pass over the edge may in practice be just slightly more than one revolution of the wafer or one pass over the edge. For example, in order to ensure that the entirety of the edge of the wafer is sampled, a single pass or revolution may include sampling the starting location of the pass or revolution again at the end of the sampling. Therefore, a system that is described herein as performing edge/notch detection or other operations in 1 revolution may actually, in practice, perform those function(s) in 1.01 revolutions of the wafer. In any case, the embodiments described herein are configured to perform edge/notch detection and possibly other functions in less than 2 revolutions or passes which is far fewer than the revolutions or passes needed by currently used systems for edge/notch detection.

The system also includes a detector configured to detect light from the spot while the spot is being scanned over the edge and to generate output responsive to the detected light. For example, as shown in FIG. 1, the system includes detector 116 configured to detect light from the spot while it is being scanned over the edge. As described further herein, the spot on the edge of the wafer illuminated by the systems described herein extends beyond the edge of the wafer. In addition, the detector (and any other detectors) described herein may be configured such that its object plane is centered on (or at least entirely located within) the illuminated spot. For example, as shown in FIG. 1, detector 116 may be configured such that light from object plane 118 is imaged onto the detector. As further shown in FIG. 1, object plane 118 may be positioned entirely within spot 104 and may have different characteristics such as size and shape than the spot. For example, the object plane may have a line shape while the spot may have a round or oval shape. In addition, both dimensions of the object plane may be less than the corresponding dimensions of the illuminated spot. As such, the object plane may not overlap with the illuminated spot near the edges of the spot where the illumination intensity may vary somewhat. In any case, in the embodiments described herein, the object plane of the detector should preferably, like the illuminated spot, extend beyond the edge of the wafer such that the edge of the wafer corresponds to a boundary in the output generated by the detector (e.g., between dark and bright areas) that can be used to determine wafer inspection coordinates of the edge as described further herein.

The detector of the embodiments described herein may be one of the multi-channel detectors described herein, which will be capable of detecting edge and notch position in a single acquisition. For example, in one embodiment, the detector is a multi-pixel detector. In this manner, the embodiments described herein may use a multi-pixel sensor for edge and notch detection.

In another embodiment, the detector is a linear detector. In this manner, the embodiments described herein may include a line sensor. For example, in a preferred embodiment, the detector may be a line sensor such as a charge coupled device (CCD) or complementary metal oxide semiconductor (CMOS) detector that includes a number of pixels to match the resolution of the collection optics. In one example, the detector may be a line array that includes 1536 pixels by 1 pixel. The detector may include different numbers of pixels (e.g., 2048 pixels) and the actual number of pixels used may be determined based on other parameters of the system (such as the bandwidth of the electronics used for processing output of the pixels). Line scan cameras that are suitable for use in the embodiments described herein are commercially available from suppliers such as Teledyne DALSA Inc., Waterloo, Ontario, Canada.

In some embodiments, the detector includes a two-dimensional array of pixels. In one such embodiment, the detector is configured to operate in a time delay integration (TDI) mode. For example, the detector may be a CCD array configured to operate in a TDI mode. In another such embodiment, the detector is configured to operate in a frames mode. For example, the detector may be a CCD array configured to operate in a frame mode.

In a further embodiment, the detector is a position sensitive detector (PSD) configured to generate the output based on spatial distribution of the light falling on the detector. For example, the detector may be a PSD, which does not necessarily have multi-pixel output, but is sensitive to the spatial distribution of light falling on the sensor and is able to provide information to find a boundary between "bright" and "dark" illuminated areas in a single pass.

In one embodiment described above in which the light directed to the spot on the edge of the wafer includes substantially collimated light, the wafer and the edge of the wafer prevent the light from the first portion of the spot from being detected by the detector, and the detector is configured such that the light from the second portion of the spot is detected by the detector. In this manner, the embodiments described herein may be configured for "beam-through" illumination of a wafer surface. For example, beam-through illumination may be generally defined as a collimated light source that sends parallel or substantially parallel rays of light from below/behind (or above/in front of) a wafer. The rays that are blocked by the wafer do not reach the detector. The rays that pass through to the detector illuminate an area on the detector. In this manner, in a "through-beam" illumination configuration, the illumination will be partially blocked from reaching the detector due to the wafer. Therefore, the border between "dark" and "bright" pixels or areas on the detector will correspond to the border of the wafer, e.g., a wafer edge or notch.

The embodiment shown in FIG. 1 is configured for such illumination and detection. For example, as shown in FIG. 1, light source 100 is configured to direct light to one side of the wafer and detector 116 is positioned on the other side of the wafer. In this manner, the portion of the spot that is incident on the wafer and the edge of the wafer will be prevented from reaching the detector by the wafer and the edge. In contrast, the portion of the spot that extends beyond the edge of the wafer and is therefore not incident on the wafer and the edge will not be blocked by the wafer and will therefore be detected by the detector.

In some embodiments, the light from the spot that is detected by the detector includes specularly reflected light. In this manner, the embodiments described herein may be configured for reflection from a wafer surface. For example, the illumination subsystem and the detector may be configured for reflection from a surface with a normal or substantially normal illumination beam that is collinear with a collection (reflected) beam path. In this manner, the illumination beam may be merged in space with a collection beam via a beam splitter. For example, as shown in FIG. 2, light from light source 202 may be merged in space with light from spot 104 by beam splitter 206. Alternatively, an illumination beam may fall on a surface at an oblique angle of incidence so that the illumination and collection beams are separated in space and do not require a beam splitter. For example, as shown in FIG. 2, light sources 200 and 204 may be configured to direct light to the spot at an oblique angle of incidence and the light from the spot that is detected by detector 116 may be collected at a different angle that is separated in space from the angles of incidence. In such configurations, the angle of incidence of the illumination beam may be close (but not necessarily close) to normal. One such configuration is shown in FIG. 2 as the configuration of light source 200. In another alternative, the illumination subsystem and detector may be configured for a dark field (DF) configuration in which an illumination beam has a relatively large angle of incidence, but the collection system uses a scattered signal and therefore is not necessarily a specular (direct reflection) order. Such a configuration is shown in FIG. 2 by light source 204 that is shown to direct light to the spot at a relatively large angle of incidence while the light from the spot is collected by collector 120 and directed to detector 116 at a non-specular angle.

In another embodiment, the light from the spot that is detected by the detector includes scattered light. For example, the illumination subsystem and detector configuration may be configured to use normal or substantially normal illumination with a relatively low numerical aperture (NA) beam (i.e., a "pencil" beam) and a collection system that collects non-specular light that is scattered at a non-zero angle with respect to normal. In one such example, light source 200 may be configured to direct light to the spot on the edge of the wafer at a normal or substantially normal illumination angle with a relatively low NA, and collector 120 may be configured to collect non-specularly reflected light that is scattered from the spot.

In some embodiments, the system may include imaging collection optics. For example, as shown in FIG. 1, the system may include collector 120 that is configured to collect light from the spot on the wafer and to direct (focus) that collected light to detector 116. Although the collector is shown in FIG. 1 as one refractive optical element, the collector may include one or more refractive and/or one or more reflective optical elements configured to collect light from the spot. Examples of suitable collectors for use in the embodiments described herein are commercially available from suppliers such as Edmund Optics Inc., Barrington, N.J. The imaging collection optics may include one or more other optical elements such as beam splitter(s), spectral filter(s), spatial filter(s), polarizing component(s), aperture(s), and the like positioned in any appropriate location in the path of the light from the wafer.

In any case, an edge and notch detection system such as that described herein is required to support samples of non-zero thickness (due to the illumination being over the edge of the wafer and therefore illuminating surfaces (such as the upper surface of the edge, the bevel, and the apex) that have different positions with respect to the optics of the system). Therefore, the depth of focus (DOF) of the optics is preferably sufficiently large to support wafer sample curvature near the edge. At the same time, the collection optics preferably provide sufficiently high resolution in order to resolve the edge and notch. DOF is proportional to inverse square of NA and to wavelength. In other words, DOF=±λ/(NA^2). Resolution is proportional to inverse NA and to wavelength. In other words, resolution=0.61λ/(NA). As such, due to conflicting requirements for NA (large for best resolution, small for DOF), generally, imaging collection optics will have a wavelength that is as short as practical with an NA selected to match DOF and resolution requirements. In other words, the wavelength(s) used for edge detection may be selected to be the lowest practical wavelength(s) and then the NA may be selected based on the selected wavelength(s) for the largest DOF and the highest resolution. For example, to achieve a DOF of greater than ±160 um with a wavelength of 405 nm, an NA of 0.05 may be selected (DOF≅0.405/0.05^2=±162 um) and that configuration also provides a resolution of R≅0.61*0.405/0.05≅5 um. In this manner, an NA of about 0.05 for imaging may be selected to balance the DOF and resolution for a given wavelength. However, the NA that is suitable for the embodiments described herein may be from about 0.04 to 0.07. The embodiments described herein may, therefore, include relatively low NA imaging optics. In addition, the DOF that the systems described herein are configured for may vary from 100 um to 300 um. Suitable resolutions for the embodiments described herein may also vary from 4 um to 7 um. The embodiments described herein also may or may not be configured for different magnifications and pixel sizes on the wafer versus detector. In one example, the system may be configured for a 2× magnification. Therefore, if the pixel size on the wafer is about 5 um, then the pixel size on the detector would be about 10 um. Obviously, however, other pixel sizes at the detector and wafer are possible.

In some embodiment, there are no optical elements positioned between the detector and the wafer. For example, in the case of an extremely low NA collimated illumination through-beam and with the detector placed sufficiently close to a wafer surface, imaging optics may be avoided altogether with the through-beam directly illuminating the sensor surface.

It is important to note that although two specific configurations are shown in FIGS. 1 and 2, the optical elements shown in these figures may be configured in a number of different arrangements to provide the same capability described herein. For example, in the case of the configuration shown in FIG. 1, the sides of the wafer on which light source 100 and detector 116 (and their associated optical elements) are positioned may be reversed. In other words, the illumination subsystem may be configured such that the light is directed to the spot on the edge of the wafer from above the wafer while the detector may be positioned under the wafer to detect light that is not blocked by the wafer.

In another configuration, the system may include detectors on both sides of the wafer (not shown) and the detectors may be configured to detect different kinds of light from the spot due to illumination with different light sources. For example, one detector may be configured to detect light that is not blocked by the wafer (for edge/notch detection) while another detector may be configured to detect scattered, or non-specularly reflected, light (for edge/notch detection and/or for inspection, which may be performed as described further herein).

The system embodiments described herein may also be configured to have a number of different light sources and/or detectors and the specific light source/detector combinations that are used for any one wafer may be determined based on the wafer. As such, not all of the light sources and/or detectors included in the system may be used for edge/notch detection and/or edge inspection for any one wafer. In this manner, the configuration of the system may be "flexible" in that the configuration used for any one wafer can be changed on a wafer-to-wafer basis, which may be advantageous if the wafer inspection system will be used to inspect wafers having different reflectivities at or near the edge of the wafer, which may be caused by the effects of polishing processes on the wafers.

Figure 3:
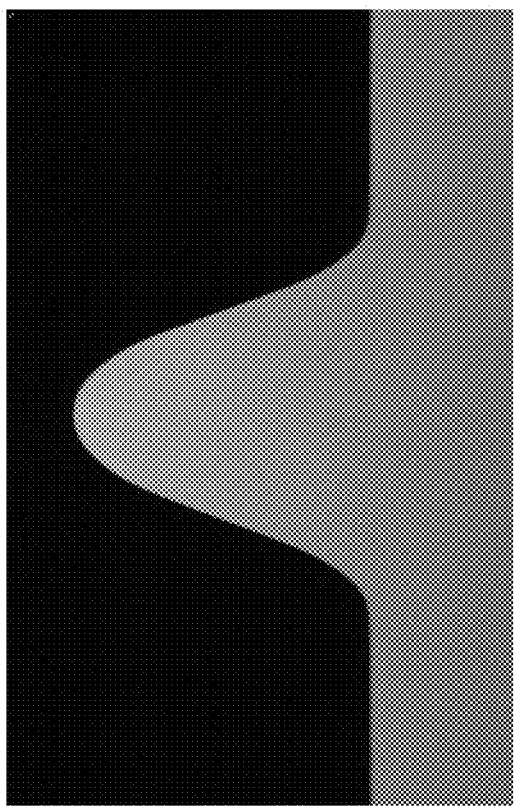
FIGS. 3-5 are examples of images that could be generated by one or more system embodiments described herein.
Figure 4:
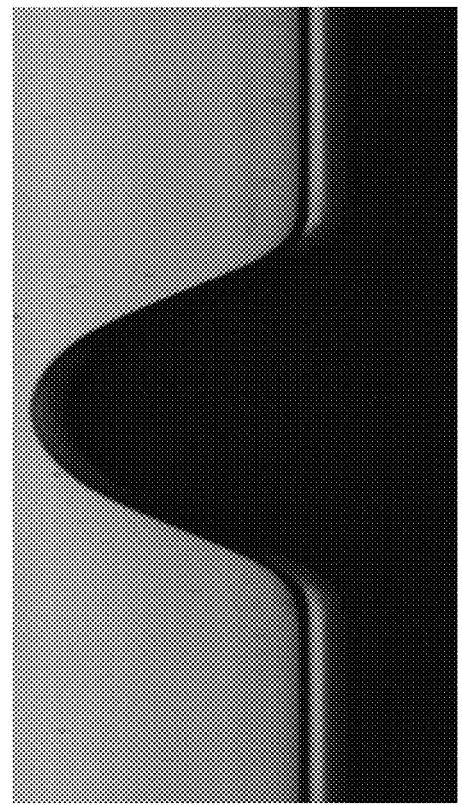
Figure 5:
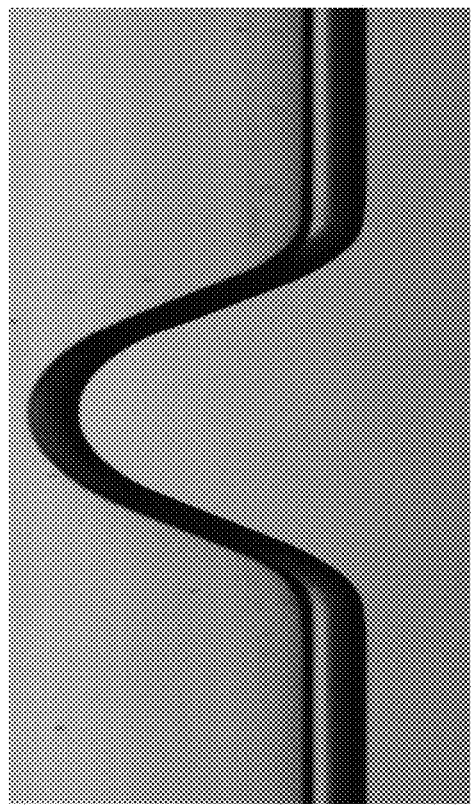

FIGS. 3-5 are images generated by a prototype system configured according to various embodiments described herein. The images shown in these figures are not meant to limit the embodiments described herein to any particular images that are generated by the system or any particular image characteristics of the images that can be generated by the system. Instead, these images are included herein to generally illustrate the type of images that could be generated by various embodiments of the system to thereby further understanding of the embodiments described herein.

The image shown in FIG. 3 is an image that was detected by an edge detection system configured as described herein. In this configuration, collimated light was directed to a spot on the edge of the wafer as described herein such that the spot extends beyond the edge of the wafer. To generate this image, light was directed to the spot from below the wafer. In addition, the detector was positioned on the opposite side of the wafer. In this manner, the light was directed to one surface of the wafer and the light from the other, opposite surface of the wafer was detected. As such, the light that is not blocked by the wafer was detected by the detector. Therefore, in this image, the lighter portion corresponds to light from the portion of the spot that extends beyond the edge of the wafer and is detected, and the darker portion corresponds to the portion of the spot that was blocked by the wafer and the edge of the wafer. In this manner, the boundary between the light and dark portions of the image shown in FIG. 3 corresponds to the edge of the wafer. The system configuration shown in FIG. 1 can therefore be used to generate images such as that shown in FIG. 3.

In contrast, the image shown in FIG. 4 is an image that was detected by a different edge detection system configured as described herein. In this configuration, light was directed to a spot on the surface of the wafer from above the wafer at both normal and oblique angles of incidence. This spot also extends beyond the edge of the wafer. In this manner, the illumination will be incident on the front side of the wafer, the edge, and the top bevel of the edge. The detector that formed this image was positioned on the side of the wafer that the illumination was directed to. Therefore, the detector detected light reflected from the spot on the wafer (which may include specularly reflected light, non-specularly reflected light, and scattered light). As such, in this image, the light portions correspond to the upper surface of the wafer and the edge of the wafer including the top bevel. The dark section of the image, extending inward from the right hand side of the image, corresponds to the portion of the spot that extends beyond the edge of the wafer and is therefore not returned from any portion of the wafer. In this manner, the boundary between the light and dark portions of the image shown in FIG. 4 corresponds to the edge of the wafer. In addition, since this image includes light from the top surface of the wafer and the edge of the wafer including the top bevel, this image may be used for inspection of the top surface, the edge, and the top bevel, which may be performed as described further herein. A system configuration that includes, for example, light sources 202 and 204 and detector 116 as shown in FIG. 2, and possibly other elements shown in FIG. 2, may be used to generate such an image.

The system embodiments described herein may also be configured to generate images at different perspectives simultaneously thereby generating a kind of "composite image." One example of such an image is shown in FIG. 5. This image was generated using both of the system configurations described above that were used to generate the images shown in FIG. 3-4. In this manner, the image was generated using illumination from below the wafer, normal or substantially normal angle of incidence illumination, and oblique angle of incidence illumination of the spot. One detector was used to simultaneously detect the light coming up from below the wafer that is not blocked by the wafer as well as the reflected (specularly and non-specularly) light and scattered light.

Therefore, in this image, the lighter portion of the image on the left side of the dark boundary corresponds to the top surface of the wafer, and the lighter portion of the image on the right side of the dark boundary corresponds to the light that comes up from below the wafer that is not blocked by the wafer or the edge. The left side of the dark boundary corresponds to the top edge of the wafer, and the right side of the dark boundary corresponds to the bottom edge of the top bevel. Any light portions contained within the dark boundary correspond to the top bevel of the edge. Therefore, a system configuration that can generate such an image may include, for example, light sources 100, 202, and 204, and detector 116 as shown in FIG. 2, and possibly other elements shown in FIG. 2.

Since the image shown in FIG. 5 clearly shows the edge of the wafer, this image can be used for edge detection as described further herein. In addition, since the image shown in FIG. 5 is responsive to light from the top surface, edge, and bevel of the wafer, this image may also be used for inspection of the top surface, edge, and bevel, which may be performed as described further herein. In this manner, the embodiments described herein that are configured for edge detection can also be configured for top surface and bevel inspection while performing edge detection, just by adding normal and oblique illumination.

The system also includes a computer processor. For example, as shown in FIG. 1, the system includes computer processor 122. Such a processor may also be included in the system shown in FIG. 2. Computer processor 122 is configured to acquire the output generated by detector(s) of the system. For example, output generated by the detector(s) during scanning may be provided to computer processor 122. In particular, the computer processor may be coupled to each of the detector(s) (e.g., by one or more transmission media shown by the dashed line in FIG. 1, which may include any suitable transmission media known in the art) such that the computer processor may receive the output generated by the detector(s). The computer processor may be coupled to each of the detectors in any other suitable manner. The computer processor may be further configured as described herein (e.g., as a processor included in a computer subsystem or system).

In one embodiment, the computer processor is configured to detect a notch formed in the edge of the wafer based on the output, and one or more parameters of the detector are configured based on sampling required to detect the notch. The notch may be detected by the computer subsystem in a number of different ways. For example, based on information about the notch such as expected dimensions and/or shape, the computer subsystem can search images such as those shown in FIGS. 3-5 for variations in the boundary in the images (the boundary corresponding to the edge of the wafer) that match or substantially match the characteristics of the notch. In one such example, based on information about the depth of the notch into the wafer, variations in the boundary having similar dimensions may be identified by the computer processor as corresponding to the notch. The computer processor may use any suitable method and/or algorithm to detect the notch in the output of the detector(s) described herein or in any other suitable manner.

The line rate of the detectors described herein may be selected to provide sufficient sampling to detect the notch. In particular, the resolution of the system in the radial direction of the wafer may be determined as described above based on the parameters of the optics included in the system such as wavelength and pixel size, while the line rate of the detectors may determine the resolution of the system in a tangential direction (i.e., the direction substantially perpendicular to the radius of the wafer). In other words, the line rate may determine how frequently output is generated at locations on the edge (i.e., the sampling frequency). More specifically, a higher line rate allows for higher sampling frequency and therefore higher tangential resolution. In one such example, the line rate of the detector may be about 100 kHZ at 8 bits.

The resolution of the system in the tangential direction can also be altered by changing the rate at which the wafer is rotated. For example, a higher resolution in the tangential direction can be enabled by a slower rate of rotation. To give an example of how line rate and rotation speed can affect the resolution, a 300 mm wafer has a circumference of about 942 mm. A wafer inspection system may be configured to rotate the wafer at different speeds, a lower one for higher sensitivity (HS) and a higher one for higher throughput (HT). As such, a detector having the same line rate for both rotation speeds will generate more samples per um (or other unit dimension) across the entire circumference of the wafer for the HS rotation rate than for the HT rotation rate. As a result, for the HS rotation speed, the circumference will be divided into more samples than for the HT rotation speed meaning that the samples will have smaller dimensions for the HS rotation speed compared to the HT rotation speed.

In one embodiment, the computer processor is configured to determine wafer inspection coordinates of a notch formed in the edge of the wafer based on the output of the detector. For example, once the notch has been detected as described above, the wafer inspection coordinates of the notch can be determined based on information about where in the scanning the output corresponding to the notch was generated as well as information about the scanning itself (e.g., the positional coordinates generated by a scanning subsystem such as one including the stage described herein during scanning of the wafer). The term "wafer inspection coordinates" as used herein refers to any coordinates that are determined by a wafer inspection system. The wafer inspection coordinates may be determined by a wafer inspection system with respect to different reference points. In addition, different wafer inspection systems may determine coordinates in different systems (e.g., polar vs. Cartesian, although since the embodiments described herein are particularly useful for spiral scanning type systems, the wafer inspection coordinates used in the embodiments described herein may be more likely to be expressed in the polar coordinate system). In any case, the term "wafer inspection coordinates" refers to any coordinates that can be generated by a wafer inspection system or subsystem included therein.

The computer processor is configured to determine wafer inspection coordinates of two or more locations on the edge of the wafer based on the output and to determine wafer inspection coordinates of one or more fixed locations on the wafer based on the wafer inspection coordinates of the two or more locations on the edge. For example, since the embodiments described herein are configured to generate an image of the wafer edge area, the computer processor may be configured to analyze the output of the detector with an appropriate algorithm and/or method to determine differences in signal from the wafer and the surrounding area. In particular, since the edge of the wafer will correspond to the boundary between the dark and bright portions of the output generated by the detector, information about that boundary can be used to detect the edge and determine information about the wafer edge such as wafer inspection coordinates. In this manner, the computer processor may be configured to use an algorithm and/or software to process data from the detector, synchronize it with the physical sample orientation, and provide edge and notch position information in the coordinate system of interest. Such algorithm and/or software may have any suitable configuration known in the art.

In some instances, the embodiments described herein may be configured to determine wafer inspection coordinates of as many locations on the edge as there are samples taken by the embodiments described herein. In this manner, the wafer inspection coordinates may be determined for many more than two locations on the edge of the wafer, and those locations can span the entire or nearly the entire edge of the wafer. However, in some instances, many fewer wafer inspection coordinates may be determined for the edge while still providing sufficient information for additional functions described herein (e.g., determining the center of the wafer). For example, if the wafer inspection coordinates for two locations on the edge of the wafer that are known to be diametrically opposed (i.e., on opposite ends of an imaginary line drawn through the center of the wafer) can be determined, those wafer inspection coordinates can be used as described further herein for determining the wafer inspection coordinates of one or more fixed locations on the wafer.

In one embodiment, the one or more fixed locations include a center of the wafer. For example, once the wafer inspection coordinates of at least two locations on the edge of the wafer have been determined, additional information about the wafer such as the wafer inspection coordinates of the wafer circumference or the wafer inspection coordinates of a wafer diameter can be determined. That information can then be used to determine the wafer inspection coordinates of the wafer center in any suitable manner based on the relationship between 1) the circumference of a circle and the center of the circle; or 2) the diameter of a circle and the center of the circle.

In some embodiments, the computer processor is configured to determine wafer inspection coordinates of defects detected on an upper surface of the wafer based on the wafer inspection coordinates of the one or more fixed locations. For example, the wafer edge/notch detection performed by the systems described herein may be part of a wafer inspection process performed on the wafer. In some such instances, the wafer edge/notch detection may be performed prior to inspecting the upper surface for defects, but the scans may be performed in reverse order as well.

For edge detection performed prior to wafer inspection, once a wafer is loaded into the wafer inspection system, the system may begin to spin the wafer to the edge scanning speed, which may be an HS or HT scanning speed as described above. As the system starts to rotate the wafer, the stage described herein may move the wafer in the x and/or y directions to position the wafer edge under and within the spot. Once the wafer edge is so positioned and the wafer is spinning at the edge scanning speed, the light may be directed to the spot and detected from the spot as described herein for edge detection performed with 1.01 rotations of the wafer at the edge detection speed.

The output generated during the edge detection scan (e.g., edge detection image data) may then be transferred to a computer processor or storage medium coupled to the computer processor. When the data transfer has finished, the computer processor may calculate the center of the wafer coordinates as described herein based on the edge detection data.

Once the edge detection and data transfer for the 1.01 rotations have completed, the wafer inspection system may start a scan of the upper surface of the wafer at the wafer inspection speed, which may be same as the edge scan speed used for edge detection. The data generated by this scan (e.g., defect data) may be stored into a buffer. Once the center of the wafer has been calculated, the oblique scan data stored in the buffer may be used with the center of wafer information to perform mapping of the reported defect coordinates using the center of wafer information and x/y calibration data. In other words, a mapping, offset, transform, or other relationship between the wafer inspection coordinates of the center of the wafer reported by the inspection system and the wafer inspection coordinates determined by the system embodiments described herein may be determined and then used to translate the wafer inspection coordinates reported for defects by the inspection system into corrected wafer inspection coordinates based on the mapping, offset, transform, or other relationship determined by the embodiments described herein. In addition, the corrected coordinates may be determined with respect to the center of the wafer or another fixed location on the wafer such as the notch. In other words, the center or notch of the wafer may be used as the origin for the corrected coordinates. In any case, the corrected coordinates are preferably determined with respect to a fixed location on the wafer such that those coordinates and the coordinates of the fixed location on the wafer determined by another system such as a defect review system can be used to relocate the defects in another process such as defect review.

In a further embodiment, the light source, the at least one optical element, and the detector are configured such that the wafer inspection coordinates of the two or more locations are determined with a precision equal to or less than 1 um. In this manner, the embodiments described herein can be used for next generation tools due to their less than 1 um edge and notch detection precision with a total detection time of less than 1 second. Typically, the precision requirements are driven by the need of review tools such as the eDR series of tools commercially available from KLA-Tencor, Milpitas, Calif. Higher precision of a wafer inspection system allows a review system to dramatically reduce the time spent searching for defects of interest (DOIs) reported by wafer inspection systems.

The embodiments described herein, therefore, provide different information than that which can be provided by wafer alignment subsystems of wafer inspection tools. For example, physical sample orientation may be typically defined by alignment procedures, alignment hardware such as a wafer pre-aligner, and a stage. Therefore, alignment procedures and hardware may provide information about notch position and require certain information about wafer edge position for their own operation. For example, the wafer center has to coincide with the stage center to within a hundred or a few hundred microns. In contrast, the embodiments described herein are configured to provide more accurate information about edge and notch position, i.e., a detection precision of roughly 1 um. Therefore, the embodiments described herein provide improved resolution thereby allowing for improved precision and accuracy of edge/notch detection.

In some embodiments, the detector is configured to detect reflected or scattered light from the spot, and the computer processor is configured to detect defects on the edge of the wafer based on the output. For example, in addition to edge and notch detection, some edge inspection capability may be provided by the embodiments described herein. In particular, the embodiments described herein provide edge inspection capability due to their relatively high resolution imaging optics and multi-channel detector. In one such example, for the optical configurations described herein, a higher resolution in the tangential direction (i.e., along the circumference of the wafer) can be provided with a slower rate of rotation, e.g., up to 4× slower in the HS operation compared to the HT operation described herein. Such slower rotation can provide for a relatively high resolution (e.g., 5 um) thereby making the system suitable for edge inspection of the wafer. All of the configurations that detect reflected or scattered light from the spot may be used for that purpose.

The computer processor may be configured to detect the defects on the edge of wafer in any suitable manner using any suitable defect detection method(s) and/or algorithm(s). For example, the output generated by the detector may be compared to a threshold and any of the output having a value above the threshold may be identified as a potential defect while the output that does not have a value above the threshold may not be identified as corresponding to potential defects. The value of the output that is compared to the threshold may include, for example, intensity. Appropriate values of the threshold may be determined in any suitable manner (e.g., as some multiple of the expected noise on the wafer edge). However, many other defect detection methods and/or algorithms are possible and the method and/or algorithm that is used with the output may be selected and/or determined based on the characteristics of the output possibly in combination with characteristics of the wafer and/or defects of interest on the wafer. Once the defects have been detected on the edge of the wafer, the wafer inspection coordinates for the edge defects can be determined and possibly corrected as described further herein.

In some such instances, once a wafer is loaded into the wafer inspection system, the system may begin to spin the wafer to the edge scanning speed, which may be an HS or HT scanning speed as described above. As the system starts to rotate the wafer, the stage described herein may move the wafer in the x and/or y directions to position the wafer edge under and within the spot as described herein. Once the wafer edge is so positioned and the wafer is spinning at the edge scanning speed, the light may be directed to the spot and detected from the spot as described herein for edge inspection performed with 1.01 rotations at the edge scanning speed.

The output generated during the edge inspection scan (e.g., edge inspection image data) may then be transferred to a computer processor or storage medium coupled to the computer processor. When the edge inspection data transfer has finished, the computer processor may process the data to detect defects on the wafer edge, which may be performed as described herein. The system may also decimate the edge inspection data to identify and then transfer only the edge defect images or data to the computer processor. Once the edge data transfer is finished, the computer processor may calculate the center of wafer coordinates based on the edge detection data.

Once the edge detection and data transfer for the 1.01 rotations have completed, the wafer inspection system may increase the wafer edge scanning speed to match the wafer inspection speed and then start a scan of the upper surface of the wafer at the wafer inspection speed. The data generated by this scan (e.g., defect data) may be stored into a buffer. Once the center of the wafer has been calculated, the oblique scan data stored in the buffer may be used with the center of wafer information to perform mapping of the reported defect coordinates using the center of wafer information and x/y calibration data, which may be performed as described further herein.

In another embodiment, the system includes an additional detector configured to detect reflected or scattered light from the spot and to generate output responsive to the detected reflected or scattered light, and the computer processor is configured to detect defects on the wafer based on the output generated by the additional detector. For example, inspection capability may be enhanced by introducing multiple detectors and collection optics arrangements. In one example, one or two of light sources 200, 202, and 204 shown in FIG. 2 may be configured as an additional detector that is configured to detect reflected and/or scattered light from the wafer edge due to illumination by at least one of the light sources. However, all of the light sources shown in FIG. 2 may remain light sources, and the system may include an additional detector (not shown) that is configured to detect light that is scattered and/or reflected from the spot due to illumination of the spot by one or more of light sources 200, 202, and 204. In some instances, the additional detector(s) may be positioned in the plane of incidence (as "top," "front," or "back" collectors in the instances of scattered light) for detection of reflected and/or scattered light or out of the plane of incidence (as "side" collectors) for detection of non-specular light. The additional detector(s) may be further configured as described herein with respect to detector 116. Detector 116 and the additional detector(s) may have substantially the same configuration or different configurations. For example, detector 116 may be configured as a linear sensor while the additional detector(s) may be configured as two-dimensional (2D) array sensors. Each of the detectors may also be coupled to its own collector, or the detectors may share one or more collectors. Any of the other optical element(s) described herein may also be coupled to (positioned in the optical path of) the additional detector(s). The computer processor may be configured to detect defects on the wafer based on the output generated by the additional detector as described further herein.

In one such embodiment, the additional detector may be configured such that its object plane is tilted with respect to an upper surface of the wafer. For example, if inspection capability is provided by additional detector(s) and collection optics arrangements, the object planes of the individual detectors configured for this purpose may be tilted with respect to the sample top surface including detectors "looking" at the side and bottom of the wafer bevel. In this manner, if the system includes multiple detectors, one or more of the detectors may have different object planes than the other detector(s). Tilting an object plane of one of the detectors that is configured to detect light from a bevel or side of the edge may be advantageous for detectors whose output will be used to detect defects on the bevel or side. For example, if the object plane of a detector can be tilted such that it is substantially parallel to an upper bevel of the edge, the output generated by the detector may be more responsive to defects on the upper bevel thereby enabling detection of such defects with higher sensitivity.

The embodiments described herein may also include an entirely different optical subsystem configured for detection of defects on the edge of the wafer. One example of such a suitable optical subsystem is described in U.S. Pat. No. 7,280,197 to Rosengaus issued on Oct. 9, 2007, which is incorporated by reference as if fully set forth herein. The embodiments described herein may be further configured as described in this patent for edge inspection.

Edge inspection systems such as those described by Rosengaus are not, however, necessarily suitable for edge detection of wafers in a manner that the edge detection can be used to determine one or more fixed locations on the wafer (e.g., a center of wafer). For example, edge inspection systems do not necessarily illuminate a spot on the wafer that extends beyond the wafer, identify a boundary in output (generated by the systems) that corresponds to the edge of the wafer, and determine wafer inspection coordinates of the edge that can then be used to determine the center of the wafer or another fixed location on the wafer. In addition, for calculating the center of the wafer substantially accurately as described herein, the detector needs to generate output based on the wafer angular position during the rotation. However, edge inspection systems generally do not include such capability. Furthermore, the lighting schemes typically used in edge inspection systems are substantially different than those described herein and can be much more simplified in the embodiments described herein compared to edge inspection systems.

Each of the system embodiments described herein may be further configured according to any other embodiment(s) described herein. In addition, each of the system embodiments described herein may be configured to perform one or more of the method embodiments described herein.

Figure 6:
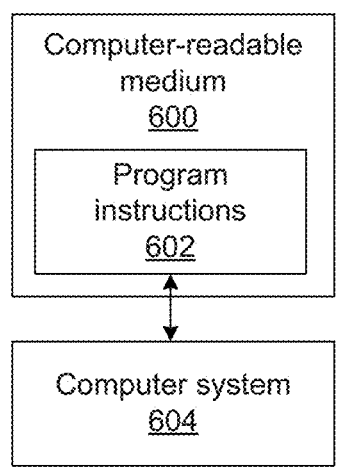
FIG. 6 is a block diagram illustrating one embodiment of a non-transitory computer-readable medium that includes program instructions executable on a computer system for performing one or more of the computer-implemented method embodiments described herein.

Another embodiment relates to a non-transitory computer-readable medium storing program instructions executable on a computer system for performing a computer-implemented method for determining wafer inspection coordinates for one or more fixed locations on a wafer described herein. One such embodiment is shown in FIG. 6. For example, as shown in FIG. 6, computer-readable medium 600 stores program instructions 602 executable on computer system 604 for performing one or more steps of the methods described herein.

Program instructions 602 implementing methods such as those described herein may be stored on computer-readable medium 600. The computer-readable medium may be a storage medium such as a magnetic or optical disk, or a magnetic tape or any other suitable non-transitory computer-readable medium known in the art.

The program instructions may be implemented in any of various ways, including procedure-based techniques, component-based techniques, and/or object-oriented techniques, among others. For example, the program instructions may be implemented using Matlab, Visual Basic, ActiveX controls, C, C++ objects, C#, JavaBeans, Microsoft Foundation Classes ("MFC"), or other technologies or methodologies, as desired.

Computer system 604 may take various forms, including a personal computer system, mainframe computer system, workstation, system computer, image computer, programmable image computer, parallel processor, or any other device known in the art. In general, the term "computer system" may be broadly defined to encompass any device having one or more processors, which executes instructions from a memory medium.

An additional embodiment relates to a method for determining wafer inspection coordinates for one or more fixed locations on a wafer. The method includes directing light to a spot on an edge of a wafer, which may be performed according to any of the embodiments described herein using any of the illumination subsystems described herein. The spot may be configured as described herein. The method also includes rotating the wafer thereby causing the spot to be scanned over the edge of the wafer, which may be performed according to any of the embodiments described herein using any of the stages described herein. As described further herein, the wafer is rotated fewer than two times while the spot is scanned over the edge. In addition, the method includes detecting light from the spot while the spot is being scanned over the edge to thereby generate output responsive to the detected light, which may be performed according to any of the embodiments described herein using any of the detectors described herein.

The method further includes determining wafer inspection coordinates of two or more locations on the edge of the wafer based on the output, which may be performed according to any of the embodiments described herein using any of the computer processors described herein. The method also includes determining wafer inspection coordinates of one or more fixed locations on the wafer based on the wafer inspection coordinates of the two or more locations on the edge, which may be performed according to any of the embodiments described herein using any of the computer processors described herein. The same computer processor may perform both of the determining steps described above.

Each of the steps of the method described above may be performed as described further herein. The method described above may include any other step(s) of any other method(s) described herein. The method described above may be performed using any of the systems described herein.

The methods described herein may also include storing results of any of the step(s) of any of the methods in a computer-readable storage medium. The results may include any of the results described herein and may be stored in any manner known in the art. The storage medium may include any suitable storage medium known in the art. After the results have been stored, the results can be accessed in the storage medium and used as described herein, formatted for display to a user, used by another software module, method, or system, etc.

Further modifications and alternative embodiments of various aspects of the invention will be apparent to those skilled in the art in view of this description. For example, methods and systems for determining wafer inspection coordinates for one or more fixed locations on a wafer are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A wafer inspection system configured to determine wafer inspection coordinates for one or more fixed locations on a wafer, comprising:
   a light source and at least one optical element forming an illumination subsystem configured to direct light to a spot on an edge of a wafer, wherein the spot extends beyond the edge of the wafer such that a first portion of the spot impinges on the wafer and the edge of the wafer and a second portion of the spot does not impinge on the wafer or the edge of the wafer;
   a stage configured to rotate the wafer thereby causing the spot to be scanned over the edge of the wafer, wherein the wafer is rotated fewer than two times while the spot is scanned over the edge;
   a detector configured to detect light from the spot while the spot is being scanned over the edge and to generate output responsive to the detected light; and
   a computer processor configured to determine wafer inspection coordinates of two or more locations on the edge of the wafer based on the output and to determine wafer inspection coordinates of one or more fixed locations on the wafer based on the wafer inspection coordinates of the two or more locations on the edge.

2. The system of claim 1, wherein the spot has at least one dimension greater than 2 mm.

3. The system of claim 1, wherein the light directed to the spot on the edge of the wafer comprises substantially collimated light, wherein the wafer and the edge of the wafer prevent the light from the first portion of the spot from being detected by the detector, and wherein the detector is further configured such that the light from the second portion of the spot is detected by the detector.

4. The system of claim 1, wherein the light is directed to the spot at a normal angle of incidence.

5. The system of claim 1, wherein the light is directed to the spot at an oblique angle of incidence.

6. The system of claim 1, wherein the light from the spot that is detected by the detector comprises specularly reflected light.

7. The system of claim 1, wherein the light from the spot that is detected by the detector comprises scattered light.

8. The system of claim 1, wherein the detector is a multi-pixel detector.

9. The system of claim 1, wherein the detector is a linear detector.

10. The system of claim 1, wherein the detector comprises a two-dimensional array of pixels, and wherein the detector is further configured to operate in a time delay integration mode.

11. The system of claim 1, wherein the detector comprises a two-dimensional array of pixels, and wherein the detector is further configured to operate in a frames mode.

12. The system of claim 1, wherein the detector is a position sensitive detector configured to generate the output based on spatial distribution of the light falling on the detector.

13. The system of claim 1, wherein there are no optical elements positioned between the detector and the wafer.

14. The system of claim 1, wherein the computer processor is further configured to determine wafer inspection coordinates of a notch formed in the edge of the wafer based on the output of the detector.

15. The system of claim 1, wherein the computer processor is further configured to detect a notch formed in the edge of the wafer based on the output, and wherein one or more parameters of the detector are configured based on sampling required to detect the notch.

16. The system of claim 1, wherein the light source, the at least one optical element, and the detector are further configured such that the wafer inspection coordinates of the two or more locations are determined with a precision equal to or less than 1 um.

17. The system of claim 1, wherein the one or more fixed locations comprise a center of the wafer.

18. The system of claim 1, wherein the computer processor is further configured to determine wafer inspection coordinates of defects detected on an upper surface of the wafer based on the wafer inspection coordinates of the one or more fixed locations.

19. The system of claim 1, wherein the detector is further configured to detect reflected or scattered light from the spot, and wherein the computer processor is further configured to detect defects on the edge of the wafer based on the output.

20. The system of claim 1, further comprising an additional detector configured to detect reflected or scattered light from the spot and to generate output responsive to the detected reflected or scattered light, wherein the computer processor is further configured to detect defects on the wafer based on the output generated by the additional detector.

21. The system of claim 20, wherein the additional detector is further configured such that its object plane is tilted with respect to an upper surface of the wafer.

22. A method for determining wafer inspection coordinates for one or more fixed locations on a wafer, comprising:
   directing light to a spot on an edge of a wafer, wherein the spot extends beyond the edge of the wafer such that a first portion of the spot impinges on the wafer and the edge of the wafer and a second portion of the spot does not impinge on the wafer or the edge of the wafer, rotating the wafer thereby causing the spot to be scanned over the edge of the wafer, wherein the wafer is rotated fewer than two times while the spot is scanned over the edge;

detecting light from the spot while the spot is being scanned over the edge to thereby generate output responsive to the detected light;

determining wafer inspection coordinates of two or more locations on the edge of the wafer based on the output; and determining wafer inspection coordinates of one or more fixed locations on the wafer based on the wafer inspection coordinates of the two or more locations on the edge, wherein the determining steps are performed by a computer processor.

* * * * *